United States Patent
Bonne et al.

(10) Patent No.: US 6,916,664 B2
(45) Date of Patent: Jul. 12, 2005

(54) FLAMMABLE VAPOR SENSOR

(75) Inventors: Ulrich Bonne, Hopkins, MN (US);
Richard W. Gehman, Freeport, IL (US)

(73) Assignee: Honeywell International Inc., Morristown, NJ (US)

(*) Notice: Subject to any disclaimer, the term of this patent is extended or adjusted under 35 U.S.C. 154(b) by 575 days.

(21) Appl. No.: 10/172,710

(22) Filed: Jun. 14, 2002

(65) Prior Publication Data

US 2003/0235925 A1 Dec. 25, 2003

(51) Int. Cl.[7] .................. G01N 33/22; G01N 27/18
(52) U.S. Cl. .................. 436/143; 73/25.03; 374/44; 422/94; 422/95; 422/96; 422/98; 436/137; 436/149; 436/151; 436/156; 436/157
(58) Field of Search ..................... 436/137, 143, 436/147, 149, 151, 155–157, 181; 422/83, 94–96, 98; 73/25.03; 374/43–44

(56) References Cited

U.S. PATENT DOCUMENTS

| | | | |
|---|---|---|---|
| 4,226,675 A | * 10/1980 | Lewis et al. ................. 376/256 |
| 4,343,768 A |   8/1982 | Kimura |
| 4,804,632 A |   2/1989 | Schuck et al. ............... 436/143 |
| 4,817,414 A | *  4/1989 | Hagen et al. ............... 73/23.31 |
| 4,944,035 A | *  7/1990 | Aagardl et al. ............. 702/136 |
| 5,168,746 A | * 12/1992 | Madhusudhan et al. ... 73/23.35 |
| 5,311,447 A |   5/1994 | Bonne |
| 5,356,819 A | * 10/1994 | Ritschel ....................... 436/147 |
| 5,401,162 A |   3/1995 | Bonne |
| 5,486,107 A |   1/1996 | Bonne |
| 5,495,747 A | *  3/1996 | Herman et al. ............. 73/23.21 |
| 5,913,343 A | *  6/1999 | Andersson .................... 141/59 |
| 6,322,247 B1 | 11/2001 | Bonne et al. |
| 6,838,287 B2 | *  1/2005 | Bonne et al. ................ 436/149 |

FOREIGN PATENT DOCUMENTS

| | | | | |
|---|---|---|---|---|
| DE | 41 12 500 A1 | 4/1991 | .......... G01N/27/18 |
| DE | 195 35 819 A1 | 9/1995 | .......... G01N/25/18 |
| DE | 10003676 | * 8/2001 | |
| EP | 139 898 | 12/1983 | .......... G01N/33/00 |
| GB | 2 333 370 A | 7/1999 | .......... G01N/33/22 |
| GB | 2 359 216 A | 10/2000 | .......... G01N/25/18 |

* cited by examiner

Primary Examiner—Arlen Soderquist
(74) Attorney, Agent, or Firm—Kermit D. Lopez; Luis M. Ortiz; Ortiz & Lopez, PLLC

(57) ABSTRACT

A method and apparatus for sensing a flammable vapor are described herein. Initially, a first thermal conductivity of a vapor at a first temperature and a second thermal conductivity of the vapor at a second temperature can be determined. Thereafter, a ratio of the first thermal conductivity signal to that of the second thermal conductivity can be calculated to obtain a primary "vapor" signal. The "vapor" ratio can then be compared to an "air" ratio of air without the vapor at the first temperature and the second temperature to obtain a secondary signal thereof. Such a secondary signal can then be compared to an alarm set-point value to thereby determine whether the vapor comprises a flammable vapor and a risk-reducing action thereof be taken.

35 Claims, 5 Drawing Sheets

FLAMMABLE VAPOR SENSOR

TECHNICAL FIELD

The present invention generally relates to sensor devices and techniques thereof. The present invention also relates to sensors for detecting vapor in air and in other gases. The present invention additionally relates to flammable vapor sensors.

BACKGROUND OF THE INVENTION

The ability to accurately detect vapor in a gas is important in many situations. For example, determining the concentration of flammable gases in a gas stream in combustion technology is important from both a safety and energy efficiency standpoint. In an organic chemical manufacturing facility, such as a refinery, for example, monitoring the concentration of vapors of certain volatile liquids in air is critical to the safety of the personnel in the area. In a home or consumer environment, the ability to automatically detect gas leakages is also critically important for protecting families and children, particularly in homes experiencing a leak in propane (LP) or natural gas lines or insufficient ventilation during work with solvents in a garage, next to an open-flame heating appliance.

Vapor sensors are particularly useful in automotive applications. As vehicle emission standards increase in stringency, engine control system designers must devise increasingly sophisticated strategies for the handling of fuel vapor generated by the evaporation of fuel contained within the tanks of the vehicle. Such fuel vapor is usually stored in one or more canisters. Each canister can be regenerated by atmospheric air flow through the canister. The resulting combined gas stream composed of air and fuel vapor is transferred into an air intake mechanism of the engine for combustion. If such regeneration of the canisters is not handled properly, the air/fuel ratio of the engine may be disturbed. This may create a problem because the tailpipe emissions of the engine or vehicle could very well increase if the resulting engine feed gas oxygen level falls outside an acceptable range.

Vapor sensors can also be utilized in fuel storage systems. Monitoring fuel storage tanks, particularly those underground, for hydrocarbon leaks is an exceedingly important environmental concern. Current detection/monitoring systems for monitoring leaks in fuel storage tanks can employ, for example, semiconductor, capacitive, and conductive liquid crystalline sensors or gas analyzers for detecting liquid or vapor leaks. These systems are complicated and very expensive.

A number of vapor sensor configurations and techniques have been attempted. Electrically conductive polymeric materials, such as conductive rubber, have been used for detecting liquid hydrocarbons, but must be placed at locations such as a sump where leaking liquid will collect and directly contact the sensor. Silicone polymer sensors have also been implemented. Silicone polymer sensors conduct electricity but are not affected by water. This type of sensor is sensitive to liquid hydrocarbon and possesses a low resistance, along with a high density of carbon black particles. This type of sensor is not responsive to gas-phase hydrocarbons.

Additional prior art sensors include combustion energy, flame ionization, gas chromatography, chemical, differential thermal analysis and optical sensors. These types of sensors are all generally expensive, complicated and are not suitable for the fabrication of detectors of flammable vapors, particular those involving hydrocarbon leaks. Still other vapor sensors are affordable and sensitive and operate using metal-oxide sensing elements but are unacceptably slow and unstable for unsupervised use over long periods of time. Thus, they are impractical and unsafe to implement.

Thus, the fast, reliable, sensitive, low-power, low-false-alarm, ambient-condition-independent and affordable detection of non-specific, flammable vapors in homes, garages, or industry presents a significant technical challenge. By way of summary of the above, prior art sensors to date can be classified generally in three categories. The first category of prior art sensors includes sensors which are low-cost and sensitive but unreliable and slow. Examples of such sensors include metal oxide or swelling-polymer type sensors. The second category of prior art sensors includes sensors which are sensitive and fast but expensive. Such sensors include IR-optical absorption type sensors. The third category of prior art sensors includes sensors which are sensitive, moderately fast and low-cost but which are unreliable and too specific to be of any use to broad sensing applications. Such sensors include electrochemical and Pellistor-type sensors, both of which are well known in the sensor arts.

Based on the foregoing, the present inventors have concluded that a need exists for a reliable and efficient flammable vapor sensor with broad applicability to a wide range of consumer and industrial situations and products. The present inventors thus are disclosing herein a solution to the aforementioned problems, which is based on a technique for sensing the presence of air-borne organic fuel vapors on the basis of their ability to change the bulk thermal conductivity properties of air and by processing this measurable change to provide an approximately universal (i.e., versus temperature and fuel type) alarm set-point relative to an LEL (Lower Explosive Limit) for any number of flammable gases or vapors.

BRIEF SUMMARY OF THE INVENTION

The following summary of the invention is provided to facilitate an understanding of some of the innovative features unique to the present invention and is not intended to be a full description. A full appreciation of the various aspects of the invention can be gained by taking the entire specification, claims, drawings, and abstract as a whole.

It is, therefore, one aspect of the present invention to provide an improved sensor method and apparatus.

It is, therefore, another aspect of the present invention to detect a vapor in air and in other gases.

It is still another aspect of the present invention to provide a flammable vapor sensor.

It is yet another aspect of the present invention to provide a sensor method and apparatus for sensing the presence of air-borne vapors on the basis of their ability to change the bulk thermal conductivities of air.

It is also an aspect of the present invention to provide a sensor method and apparatus for sensing the presence of air-borne vapors by processing a measurable change of thermal conductivity signals to provide an approximately universal alarm set-point relative to a lower-explosive limit (LEL).

The above and other aspects can be achieved as is now described. A method and apparatus for sensing a flammable vapor are described herein. Initially, a first thermal conductivity signal of a vapor at a first temperature and a second thermal conductivity signal of the vapor at a second temperature are determined. Thereafter, a vapor signal ratio of the first thermal conductivity signal to that of the second thermal conductivity signal can be calculated. The "vapor" ratio (i.e., vapor ratio) can then be compared to an "air" ratio (i.e., air ratio) of air without the vapor at the first temperature and the second temperature to obtain a calculated signal thereof. Such a calculated signal can then be compared to an alarm set-point value to thereby determine whether the vapor comprises a flammable or combustible vapor, or one that is close to becoming flammable. Note that the terms "vapor ratio" and "vapor signal ratio" may be utilized herein interchangeably. Similarly, the terms "air ratio" and "air signal ratio" may also be utilized herein interchangeably.

Accordingly, the alarm set-point value can be located in a range of values near or below a lower-explosive limit (LEL). The first thermal conductivity signal of the vapor is generally determined at the first temperature and the second thermal conductivity signal at a second temperature, wherein the first temperature can comprise 100° C. above ambient and the second temperature can comprise 200° C. above ambient. EMS These temperatures can be chosen as a compromise between generating the largest sensor signal (i.e., at the highest temperature of the heating element) and the lowest power consumption, lowest ignition hazard and longest sensor life and stability.

The thermal conductivity signals can be determined utilizing a microbridge sensor. The microbridge sensor can be initially heated to the first temperature, while the associated heater voltage, power or temperature is recorded, thereafter heated to the second temperature, while a second recording is made. The microbridge sensor may include at least one microbridge heater. Alternatively, two heaters can be used, whereby one heater is heated to one condition of temperature, applied voltage, current or power and the second heater is heated to a second-and-different condition. However, due to the potentially larger errors of this alternate approach, if the two heaters age or change or drift at unequal rates, the former approach is the preferred one.

Additionally, the aforementioned first and second thermal conductivity signals can be utilized to determine a fuel-in-air concentration of an air-fuel mixture that is less than or approximately equal to or larger than a lower-explosive limit (LEL) of the air-fuel mixture. Note that microbridge sensor heaters can include those having received Intrinsic Safety (IS) certification for operation in flammable gas mixtures of hydrocarbon (HC)-air and $H_2$-air mixtures, but not in HC—$O_2$ mixtures.

The vapor to be detected may comprise an organic vapor associated with a fuel associated with the air-fuel mixture. The air signal ratio of air without the vapor at the first temperature and the second temperature can be determined and stored within a storage area of a microprocessor (i.e., and it may be periodically updated in air, if ultimate stability and accuracy is required). Thereafter, the air signal ratio may be retrieved from the storage area of the microprocessor prior to comparing the vapor ratio to the air signal ratio to obtain the signal thereof.

The present invention thus provides a flammable vapor sensor method and apparatus for sensing the presence of air-borne vapors on the basis of their ability to change the bulk thermal conductivities of air and by processing this measurable change to provide an approximately universal (i.e., versus ambient temperature and fuel type) alarm set-point relative to the LEL. In fact, the method and apparatus described below should provide fail-safe LEL readouts that are largely immune to changes in ambient temperature, pressure, humidity and fuel type (methane, natural gas, LP (propane), liquid fuel vapors, and solvents).

BRIEF DESCRIPTION OF THE DRAWINGS

The accompanying figures, in which like reference numerals refer to identical or functionally-similar elements throughout the separate views and which are incorporated in and form part of the specification, further illustrate the present invention and, together with the detailed description of the invention, serve to explain the principles of the present invention.

DETAILED DESCRIPTION OF THE INVENTION

The particular values and configurations discussed in these non-limiting examples can be varied and are cited merely to illustrate embodiments of the present invention and are not intended to limit the scope of the invention.

Figure 1:
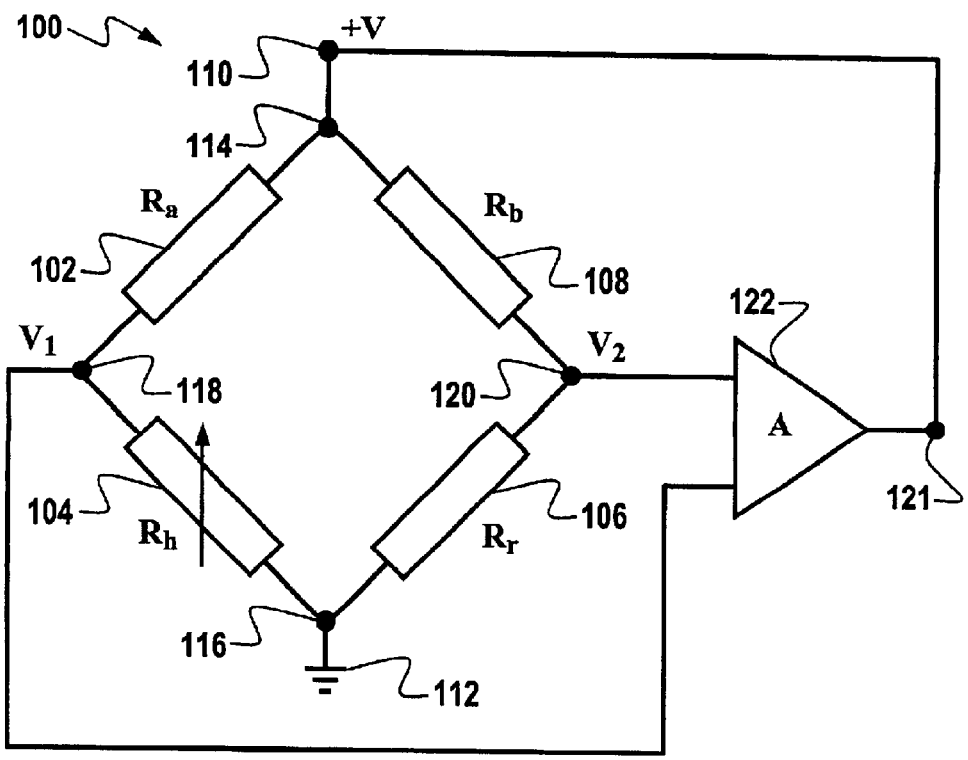
FIG. 1 depicts a schematic diagram of a thermal conductivity sensing circuit, which may be implemented in accordance with a preferred embodiment of the present invention.

FIG. 1 depicts a schematic diagram of a preferred (i.e., approximate constant temperature rise) thermal conductivity sensing circuit 100, which may be implemented in accordance with a preferred embodiment of the present invention. Circuit 100 generally includes four resistors 102, 104, 106 and 108 arranged in a microbridge configuration. Sensing circuit 100 can thus be referred to as a "heater control circuit" for a microbridge sensor. Sensing circuit 100 is generally tied to a ground 112 at a node 116, which is generally located between resistors 104 and 106. Sensing circuit 100 can be further coupled to a power supply 110 at a node 114, which is generally located between resistors 102 and 108. Power supply 110 is labeled +V in FIG. 1.

Additionally, a voltage $V_1$ can be measured at a node 118, which is generally located between resistors 102 and 104. Similarly, a voltage $V_2$ can be measured at a node 120, which is generally located between resistors 106 and 108. As also illustrated in FIG. 1, resistor 102 is labeled $R_a$ and resistor 104 is labeled $R_h$. Additionally, resistor 106 is labeled $R_r$ and resistor 108 is labeled $R_b$. An amplifier 122 is connected to node 118 and node 120, respectively $V_1$ and $V_2$. An output 121 of amplifier 122 (i.e., labeled A) is further connected to power supply 110 and node 114. Amplifier 122 can function as a high-gain operation amplifier.

Figure 2:
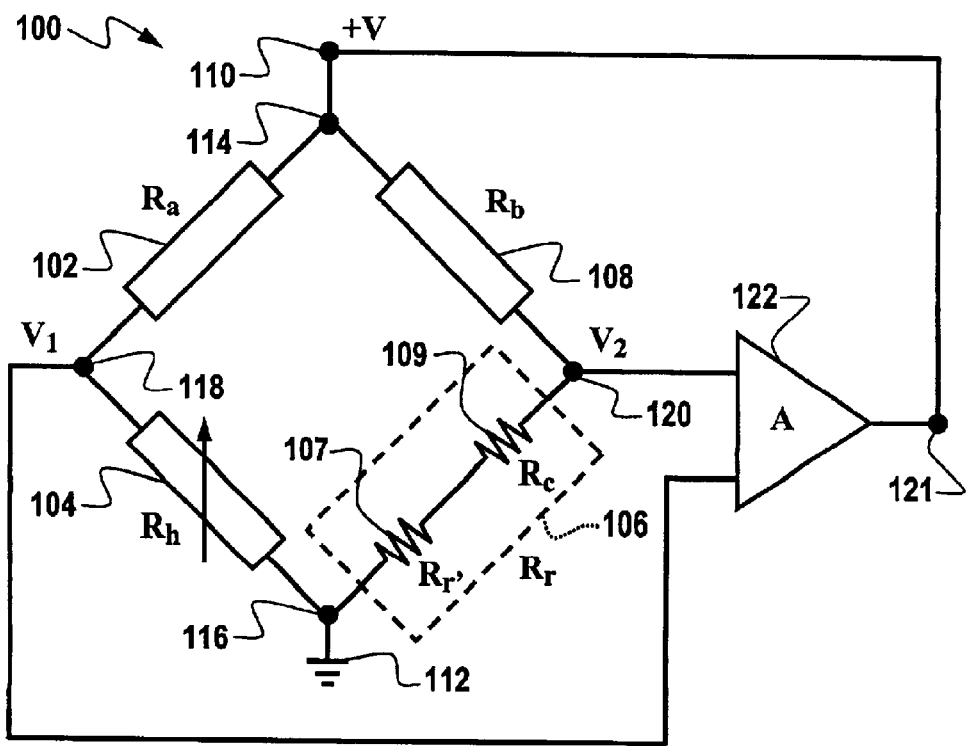
FIG. 2 illustrates a detailed view of the schematic diagram of FIG. 1.

Additionally, as illustrated in FIG. 2, resistor 106 (i.e., $R_r$) is generally composed of a resistor $R_{r'}$ (i.e., of TCR as $R_h$) and a series resistor $R_c$ of zero TCR, so that adjustment of the $R_{r'}/R_c$ ratio can achieve a minimum ambient temperature dependence of $V_1=V_2$ or V. The function of the high-gain operational amplifier (i.e., amplifier 122) is to drive $\Delta V=V_2-V_1$ to zero, by increasing V until the temperature of resistor 104 (i.e., $R_h$) is raised enough to make $\Delta V\sim 0$. Note that in FIG. 2, resistor 107 is labeled $R_r$, and resistor 109 is labeled $R_c$. Also, in FIG. 2, resistor 106 is represented as a dashed line.

FIG. 2 thus illustrates a detailed view of the circuit 100 of FIG. 1. Although resistors 107 and 109 are indicated positioned in series with one another in FIG. 2, those skilled in the art can appreciate that variations, including parallel and series modifications thereof, may be implemented in accordance with the apparatus and method disclosed herein. Note that in FIGS. 1 and 2 herein, like parts are indicated by analogous or identical reference numerals.

The invention disclosed herein thus generally describes a method and apparatus for sensing a flammable gas-air mixture. Such a gas-air mixture comprises at least one combustible component, which can be referred to herein for brevity sake as "vapor". The present invention can be implemented within an embodiment that utilizes a microbridge sensor, such as sensing circuit 100 of FIG. 1, to utilize variations in thermal conductivity (TC) to sense the amount of organic fuel vapor concentrations in air. Note that although a particular type of microbridge sensing circuit 100 is depicted in FIG. 1, it can be understood by those skilled in the art that variations to such a circuit may be implemented in accordance with the method and apparatus of the present invention. The particular sensing circuit 100 depicted in FIG. 1 generally illustrates but one type of microbridge circuit that can be implemented in accordance with the method and apparatus described herein.

Generally, the fact that the TC of organic vapors decreases as their molecular weight increases, enables an approximate correlation between the sensor signal and air-combustible gas mixture, from here on simply referred to as air-fuel mixture stoichiometry (i.e., to combust to form $CO_2$ and $H_2O$), independent of the type of fuel. The inventors have found that sensor TC-output approximately relates to the fraction of the lower-explosive limit (LEL) of an air-fuel mixture, due to the finding that the LEL concentration of vapors is generally near 50–60% of their stoichiometric concentration. Additionally, the present inventors have found that the temperature dependence of the TC of organic fuel-air mixtures even more closely relates to the stoichiometry (i.e., for either 100% combustion or LEL) of such mixtures.

Among the possible approaches of utilizing TC for the detection of fuel-in-air concentrations near their LEL, a Thermal Conductivity Ratio Difference (TCRD) approach can be implemented in accordance with a preferred embodiment of the present invention, which generally relies on the higher TC-temperature dependence of organic fuels, including methane, water vapor and carbon dioxide than that of air. Table 1 below demonstrates how well this finding holds true for a number of common combustible gases, solvents or fuels.

TABLE 1

Differences between Two-Temperature-$V_h$-Ratios of Organic Fuel-Air mixtures at Their LEL and Pure Air over Reference-Air-Ratios Adjusted to Each Temperature vs. Temperature*

| | | | | Diff.x1000 of Vh/Vh at 2-ΔTh-SPs for M&A** | | | | | |
|---|---|---|---|---|---|---|---|---|---|
| Fuel | ID | No. Cs | LEL % | −40° C. | −20° C. | 0° C. | 20° C. | 40° C. | 60° C. |
| METHANE | 9 | 1 | 5.70 | 2.31 | 2.26 | 2.21 | 2.17 | 2.13 | 2.10 |
| ETHANE | 10 | 2 | 3.40 | 2.18 | 2.13 | 2.07 | 2.02 | 1.97 | 1.92 |
| PROPANE | 11 | 3 | 2.42 | 1.53 | 1.51 | 1.48 | 1.45 | 1.42 | 1.39 |
| ISOBUTANE | 12 | 4 | 1.88 | 1.32 | 1.30 | 1.28 | 1.26 | 1.22 | 1.19 |
| BUTANE | 13 | 4 | 1.88 | 1.21 | 1.23 | 1.24 | 1.24 | 1.23 | 1.22 |
| ISOPENTANE | 14 | 5 | 1.53 | 1.14 | 1.14 | 1.13 | 1.11 | 1.10 | 1.08 |
| PENTANE | 15 | 5 | 1.50 | 1.07 | 1.07 | 1.07 | 1.07 | 1.06 | 1.05 |
| HEXANE | 16 | 6 | 1.80 | 1.72 | 1.64 | 1.58 | 1.52 | 1.47 | 1.43 |
| CYCLOHEXANE | 17 | 6 | 1.37 | 1.06 | 1.07 | 1.07 | 1.07 | 1.07 | 1.06 |
| BENZENE | 18 | 6 | 1.63 | 1.09 | 1.08 | 1.07 | 1.05 | 1.03 | 1.01 |
| HEPTANE | 19 | 7 | 1.10 | 1.05 | 1.01 | 0.97 | 0.94 | 0.91 | 0.89 |
| 2,2,3-TRIMETHYLBUT | 20 | 7 | 1.12 | 0.82 | 0.78 | 0.75 | 0.71 | 0.68 | 0.64 |
| HEPT-1-ENE | 21 | 7 | 1.18 | 0.82 | 0.81 | 0.80 | 0.79 | 0.78 | 0.77 |
| METHYLCYCLOHEXANE | 22 | 7 | 1.18 | 0.99 | 0.99 | 0.99 | 0.98 | 0.97 | 0.95 |
| TOLUENE | 23 | 7 | 1.37 | 0.90 | 0.90 | 0.89 | 0.88 | 0.86 | 0.85 |
| OCTANE | 24 | 8 | 1.00 | 0.83 | 0.83 | 0.83 | 0.83 | 0.82 | 0.81 |
| 2,2,4-TRIMETHYLPEN | 25 | 8 | 1.10 | 0.88 | 0.87 | 0.87 | 0.85 | 0.84 | 0.82 |
| OCT-1-ENE | 26 | 8 | 1.03 | 1.30 | 1.12 | 0.99 | 0.91 | 0.84 | 0.79 |
| trans-1,2-DIMETHYL | 27 | 8 | 1.03 | 0.96 | 0.96 | 0.95 | 0.94 | 0.93 | 0.91 |
| M-XYLENE | 28 | 8 | 1.18 | 0.73 | 0.73 | 0.73 | 0.72 | 0.71 | 0.69 |
| O-XYLENE | 29 | 8 | 1.18 | 0.72 | 0.72 | 0.72 | 0.71 | 0.69 | 0.68 |
| NONANE | 30 | 9 | 0.89 | 0.90 | 0.88 | 0.86 | 0.84 | 0.82 | 0.80 |
| 1,2,3-TRIMETHYLBEN | 31 | 9 | 1.03 | 0.59 | 0.60 | 0.60 | 0.60 | 0.59 | 0.59 |
| DECANE | 32 | 10 | 0.80 | 0.85 | 0.83 | 0.82 | 0.80 | 0.78 | 0.76 |
| DEC-1-ENE | 33 | 10 | 0.83 | 0.60 | 0.60 | 0.59 | 0.58 | 0.57 | 0.56 |
| METHANOL | 34 | 1 | 7.37 | 2.98 | 3.11 | 3.19 | 3.24 | 3.27 | 3.27 |
| ETHANOL | 35 | 2 | 3.30 | 1.84 | 1.81 | 1.77 | 1.73 | 1.69 | 1.64 |
| PROPAN-1-OL | 36 | 3 | 2.68 | 1.64 | 1.62 | 1.60 | 1.58 | 1.55 | 1.52 |
| BUTAN-1-OL | 37 | 4 | 2.03 | 1.28 | 1.27 | 1.26 | 1.24 | 1.22 | 1.20 |
| METHYL tertBUTYL E | 38 | 5 | 2.00 | 1.20 | 1.23 | 1.24 | 1.24 | 1.23 | 1.22 |
| ETHYL n-BUTYL ETHE | 39 | 6 | 1.37 | 0.96 | 0.95 | 0.93 | 0.91 | 0.89 | 0.87 |
| DODECANE | +40 | 12 | 0.67 | 0.75 | 0.74 | 0.73 | 0.71 | 0.70 | 0.68 |

TABLE 1-continued

Differences between Two-Temperature-$V_h$-Ratios of Organic Fuel-
Air mixtures at Their LEL and Pure Air over Reference-Air-Ratios
Adjusted to Each Temperature vs. Temperature*

| | | | | Diff.x1000 of Vh/Vh at 2-ΔTh-SPs for M&A** | | | | | |
|---|---|---|---|---|---|---|---|---|---|
| Fuel | ID | No. Cs | LEL % | -40° C. | -20° C. | 0° C. | 20° C. | 40° C. | 60° C. |
| NAPHTHALENE | +41 | 10 | 1.03 | 0.67 | 0.67 | 0.66 | 0.65 | 0.64 | 0.62 |
| 1-METHYLNAPHTHALEN | +42 | 11 | 0.92 | 0.63 | 0.62 | 0.61 | 0.60 | 0.59 | 0.57 |
| 2-METHYLNAPHTHALEN | +43 | 11 | 0.92 | 0.62 | 0.62 | 0.61 | 0.60 | 0.59 | 0.57 |
| TETRADECANE | +44 | 14 | 0.58 | 0.68 | 0.67 | 0.66 | 0.65 | 0.64 | 0.62 |
| TETRADEC-1-ENE | +45 | 14 | 0.59 | 0.37 | 0.37 | 0.37 | 0.37 | 0.37 | 0.36 |
| HEXADECANE | +46 | 16 | 0.51 | 0.61 | 0.61 | 0.60 | 0.59 | 0.58 | 0.57 |
| 2,2,4,4,6,8,8-HEPT | +47 | 16 | 0.51 | 0.36 | 0.37 | 0.37 | 0.37 | 0.37 | 0.36 |
| 2-METHYLPENTADECAN | +48 | 16 | 0.51 | 0.33 | 0.33 | 0.33 | 0.33 | 0.32 | 0.31 |
| HEPTADECANE | +49 | 17 | 0.48 | 0.26 | 0.28 | 0.28 | 0.29 | 0.29 | 0.29 |
| OCTADECANE | +50 | 18 | 0.45 | 0.25 | 0.26 | 0.27 | 0.27 | 0.27 | 0.27 |
| n-NONADECANE | +51 | 19 | 0.43 | 0.23 | 0.24 | 0.24 | 0.25 | 0.25 | 0.25 |
| n-EICOSANE | +52 | 20 | 0.41 | 0.21 | 0.22 | 0.23 | 0.23 | 0.23 | 0.23 |
| ETHYLBENZENE | 53 | 8 | 1.18 | 0.77 | 0.76 | 0.76 | 0.75 | 0.73 | 0.72 |

+ Fuels for which their concentration at 1 bar due to vapor pressure at 60° C. <LEL, so that their vapors can only become flammable in combination with others.
*TPETAvsk.U18/HC/900/950, TCRD. The chosen 2 microbridge $\Delta T_h$ were 100 and 200° C.
**The listed values are: $\{V_{h,H}(M, T)/V_{h,L}(M, T) - V_{h,H}(A, T)/V_{h,L}(A, T)\}1000$, where $V_{h,H,L} = V_h$ at high and low $\Delta T_{htr}$, respectively, and M = F + A Mixture and A = air.

It is important to note that a gaseous mixture containing one or more combustible components may be flammable if the concentrations of all the combustible components, including their individual fractional lower explosive limit (LEL) values, sum to a value of 100% LEL or greater. For example, if a gas mixture is composed of air with methane and butane, such that the methane concentration is 2 vol % (i.e., LEL=4.5 vol. %, representing a 100×2/4.5=44.4% LEL mixture) and the butane concentration is 1 vol % (i.e., LEL=1.5 vol %, representing a 100×1/1.5=66.7% LEL), the mixture is viewed as flammable because 44.4+66.7=111.1% LEL is greater than 100% LEL. Additionally, all vapors are gases. They differ from "permanent" gases in that they can be condensed by application of sufficient pressure. The term "fuel-air gas mixture" can be utilized herein instead of the more lengthy term "combustible gas/air gas mixture" or "flammable gas/air gas mixture". Note that Table 2 below indicates data collected as a result of the TCD approach described herein. Table 2 lists data indicative of differences between the TC signal of air and that of organic fuel-air mixtures at their LEL versus temperature. In Table 2, reference air-TC-signals are adjusted accordingly for each temperature. Those skilled in the art can appreciate that the information provided in Tables 1 and 2 herein are not considered limiting features of the present invention but rather are included herein for exemplary and general edification and illustrative purposes only.

TABLE 2

TCD Method: Differences between TC-Signal of Air and That
of Organic Fuel - Air mixtures at Their LEL vs. Temperature*
(Reference Air-TC-Signal Adjusted to Each Temperature)

| | | | | Duff. of V(h,A)-V(h,M) in mV at LEL in Air** | | | | | |
|---|---|---|---|---|---|---|---|---|---|
| Fuel | ID | No. Cs | LEL % | -40° C. | -20° C. | 0° C. | 20° C. | 40° C. | 60° C. |
| METHANE | 9 | 1 | 4.50 | -26.20 | -29.31 | -32.44 | -35.60 | -38.78 | -41.99 |
| ETHANE | 10 | 2 | 3.40 | 2.63 | -0.48 | -3.62 | -6.77 | -9.94 | -13.13 |
| PROPANE | 11 | 3 | 2.42 | 12.25 | 10.20 | 8.11 | 6.00 | 3.87 | 1.72 |
| ISOBUTANE | 12 | 4 | 1.88 | 15.78 | 14.10 | 12.38 | 10.64 | 8.89 | 7.13 |
| BUTANE | 13 | 4 | 1.88 | 15.42 | 13.81 | 12.13 | 10.38 | 8.59 | 6.76 |
| ISOPENTANE | 14 | 5 | 1.53 | 17.40 | 15.97 | 14.50 | 13.00 | 11.47 | 9.92 |
| PENTANE | 15 | 5 | 1.50 | 17.15 | 15.81 | 14.41 | 12.97 | 11.48 | 9.97 |
| HEXANE | 16 | 6 | 1.80 | 26.96 | 25.01 | 23.05 | 21.08 | 19.10 | 17.12 |
| CYCLOHEXANE | 17 | 6 | 1.37 | 20.18 | 18.89 | 17.53 | 16.13 | 14.68 | 13.20 |
| BENZENE | 18 | 6 | 1.63 | 25.05 | 23.84 | 22.59 | 21.31 | 20.01 | 18.70 |
| HEPTANE | 19 | 7 | 1.10 | 21.07 | 19.93 | 18.79 | 17.63 | 16.47 | 15.30 |
| 2,2,3-TRIMETHYLBUT | 20 | 7 | 1.12 | 18.11 | 17.26 | 16.42 | 15.59 | 14.79 | 14.00 |
| HEPT-1-ENE | 21 | 7 | 1.18 | 19.95 | 19.06 | 18.13 | 17.18 | 16.20 | 15.21 |
| METHYLCYCLOHEXANE | 22 | 7 | 1.18 | 19.28 | 18.10 | 16.86 | 15.59 | 14.30 | 12.98 |
| TOLUENE | 23 | 7 | 1.37 | 23.48 | 22.52 | 21.51 | 20.48 | 19.42 | 18.34 |
| OCTANE | 24 | 8 | 1.00 | 22.93 | 22.05 | 21.12 | 20.16 | 19.17 | 18.15 |
| 2,2,4-TRIMETHYLPEN | 25 | 8 | 1.10 | 20.50 | 19.52 | 18.51 | 17.48 | 16.42 | 15.35 |
| OCT-1-ENE | 26 | 8 | 1.03 | 22.18 | 21.02 | 19.94 | 18.90 | 17.90 | 16.92 |
| trans-1,2-DIMETHYL | 27 | 8 | 1.03 | 16.43 | 15.25 | 14.04 | 12.79 | 11.53 | 10.26 |

TABLE 2-continued

TCD Method: Differences between TC-Signal of Air and That of Organic Fuel - Air mixtures at Their LEL vs. Temperature*
(Reference Air-TC-Signal Adjusted to Each Temperature)

| Fuel | ID | No. Cs | LEL % | Diff. of V(h,A)-V(h,M) in mV at LEL in Air** | | | | | |
|---|---|---|---|---|---|---|---|---|---|
| | | | | −40° C. | −20° C. | 0° C. | 20° C. | 40° C. | 60° C. |
| M-XYLENE | 28 | 8 | 1.18 | 24.17 | 23.46 | 22.72 | 21.95 | 21.16 | 20.35 |
| O-XYLENE | 29 | 8 | 1.18 | 23.38 | 22.68 | 21.94 | 21.18 | 20.40 | 19.61 |
| NONANE | 30 | 9 | 0.89 | 24.24 | 23.33 | 22.40 | 21.45 | 20.48 | 19.51 |
| 1,2,3-TRIMETHYLBEN | 31 | 9 | 1.03 | 23.57 | 23.04 | 22.48 | 21.88 | 21.26 | 20.62 |
| DECANE | 32 | 10 | 0.80 | 25.09 | 24.26 | 23.41 | 22.54 | 21.66 | 20.77 |
| DEC-1-ENE | 33 | 10 | 0.83 | 22.04 | 21.51 | 20.94 | 20.36 | 19.76 | 19.16 |
| METHANOL | 34 | 1 | 7.37 | 6.83 | 2.14 | −2.79 | −7.94 | −13.27 | −18.74 |
| ETHANOL | 35 | 2 | 3.30 | 2.26 | −0.39 | −3.07 | −5.77 | −8.48 | −11.19 |
| PROPAN-1-OL | 36 | 3 | 2.68 | 7.70 | 5.40 | 3.05 | 0.67 | −1.74 | −4.18 |
| BUTAN-1-OL | 37 | 4 | 2.03 | 10.55 | 8.82 | 7.04 | 5.23 | 3.40 | 1.53 |
| METHYL tertBUTYL E | 38 | 5 | 2.00 | 24.45 | 22.98 | 21.44 | 19.84 | 18.19 | 16.50 |
| ETHYL n-BUTYL ETHE | 39 | 6 | 1.37 | 23.82 | 22.79 | 21.73 | 20.66 | 19.57 | 18.48 |
| DODECANE | +40 | 12 | 0.67 | 26.84 | 26.18 | 25.48 | 24.77 | 24.04 | 23.30 |
| NAPHTHALENE | +41 | 10 | 1.03 | 24.39 | 23.78 | 23.15 | 22.49 | 21.82 | 21.13 |
| 1-METHYLNAPHTHALEN | +42 | 11 | 0.92 | 21.84 | 21.27 | 20.67 | 20.05 | 19.42 | 18.78 |
| 2-METHYLNAPHTHALEN | +43 | 11 | 0.92 | 21.90 | 21.33 | 20.73 | 20.11 | 19.48 | 18.85 |
| TETRADECANE | +44 | 14 | 0.58 | 28.03 | 27.48 | 26.91 | 26.31 | 25.70 | 25.07 |
| TETRADEC-1-ENE | +45 | 14 | 0.59 | 22.99 | 22.81 | 22.59 | 22.35 | 22.10 | 21.83 |
| HEXADECANE | +46 | 16 | 0.51 | 29.22 | 28.78 | 28.32 | 27.83 | 27.32 | 26.79 |
| 2,2,4,4,6,8,8-HEPT | +47 | 16 | 0.51 | 20.89 | 20.67 | 20.42 | 20.15 | 19.86 | 19.56 |
| 2-METHYLPENTADECAN | +48 | 16 | 0.51 | 22.83 | 22.70 | 22.55 | 22.38 | 22.20 | 22.01 |
| HEPTADECANE | +49 | 17 | 0.48 | 23.49 | 23.44 | 23.36 | 23.25 | 23.13 | 22.98 |
| OCTADECANE | +50 | 18 | 0.45 | 23.57 | 23.55 | 23.51 | 23.43 | 23.34 | 23.22 |
| n-NONADECANE | +51 | 19 | 0.43 | 23.75 | 23.77 | 23.76 | 23.72 | 23.66 | 23.58 |
| n-EICOSANE | +52 | 20 | 0.41 | 23.81 | 23.86 | 23.87 | 23.86 | 23.83 | 23.78 |
| ETHYLBENZENE | 53 | 8 | 1.18 | 23.80 | 23.04 | 22.25 | 21.43 | 20.59 | 19.7 |

+ Fuels for which their concentration at 1 bar due to vapor pressure at 60° C. <LEL, so that their vapors can only become flammable in combination with others
*TPETAvsk.U18/HC/900/950
The chosen microbridge heater temperature rise was 200°
**The listed values are: $\{V_{h,H}(A,T) - V_{h,H}(M,T)\} \times 1000$, where $V_{h,H}$ = TC-signal at a high $\Delta T_h = 200°$ C., M = fuel + air Mixture and A = Air. Nominal $V_{h,H}$ = 4 V.

Note that circuit 100 illustrated in FIG. 1 may be modified in such a manner that voltage 110 (i.e., +V) can be generated by forcing a constant current through the Wheatstone bridge circuit (i.e., circuit 100). Such a constant current can be provided by a high impedance power supply instead of the amplifier 122 (i.e., op amp) depicted in FIG. 1. As the thermal conductivity associated with resistor 104 (i.e., $R_h$) changes, the temperatures and resistance of resistor 104 can also change, which may be indicated by a different op amp output, which constitutes an output signal. Such an approach can be referred to as a "constant current" approach.

Circuit 100 of FIG. 1 can also be modified in such a manner that the voltage 110 (i.e., +V) can be generated by applying a constant voltage through the Wheatsone bridge circuit (i.e., circuit 100). Such a constant voltage can be provided by a constant voltage power supply and not by the amplifier 122 (i.e., op am) illustrated in FIG. 1. As the thermal conductivity around resistor 104 $R_h$ changes, the temperature and resistance of resistor 104 may also change, which would be indicated by a different op amp output and thereby constitute the output signal of interest. Such an approach can be referred to as a "constant voltage" approach.

Additionally, circuit 100 of FIG. 1 can be modified in such a manner that the voltage 110 (i.e., +V) can be generated by applying a voltage X current product (i.e., provided by a constant power control circuit and not by amplifier 122) through the Wheatsone bridge circuit (i.e., circuit 100). As the thermal conductivity associated with resistor 104 changes, the temperature and resistance of resistor 104 will also change, which can be indicated by a different op amp output and thereby constitute the output signal of interest. Such an approach can be referred to as a "constant power" approach.

Figure 3:
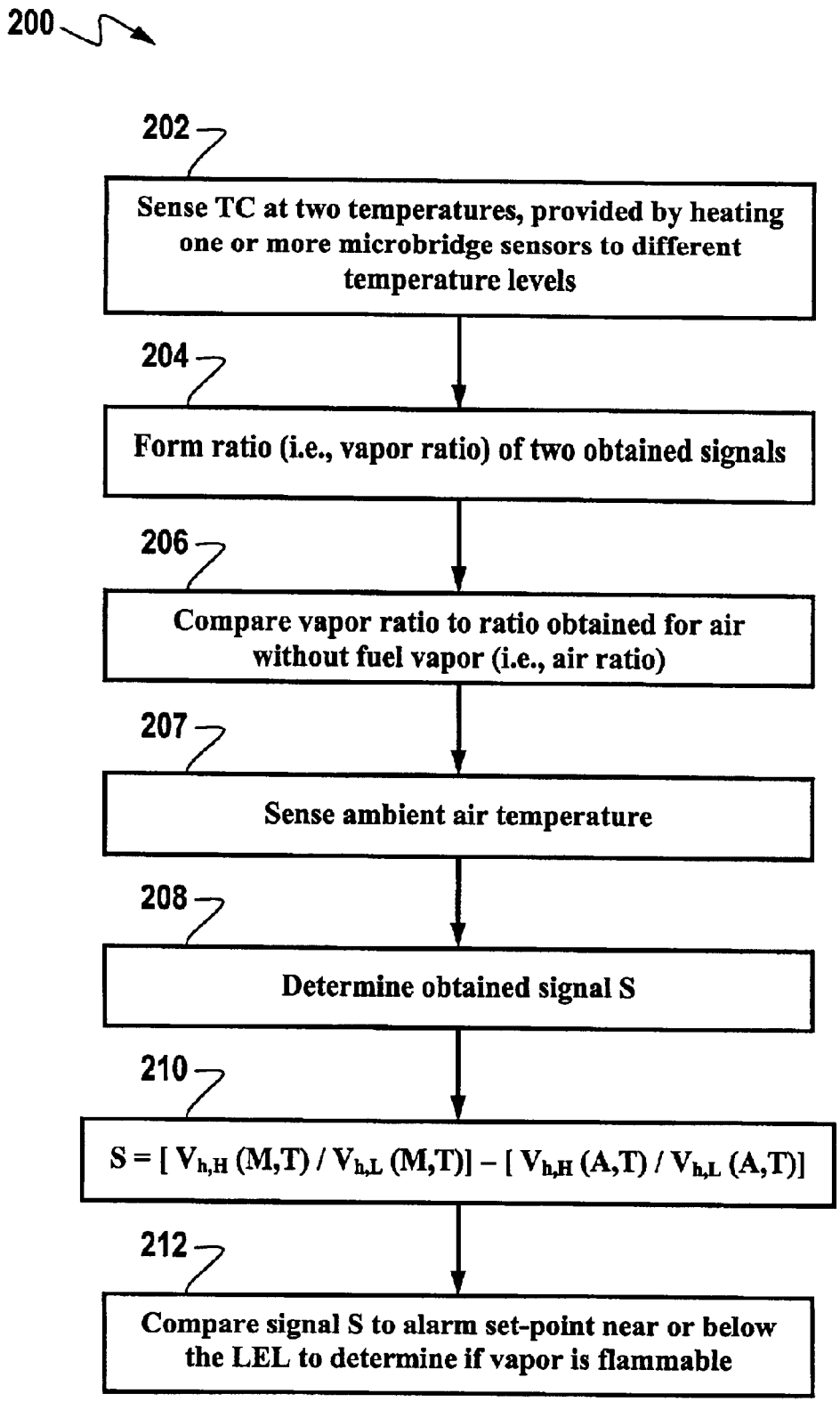
FIG. 3 illustrates a high-level flow chart of operations illustrating logical operational steps, which may be implemented in accordance with a preferred embodiment of the present invention.

FIG. 3 illustrates a high-level flow chart 200 of operations illustrating logical operational steps, which may be implemented in accordance with a preferred embodiment of the present invention. As depicted at block 202, the TC is generally sensed at two temperatures, provided by heating preferably one microbridge, but possibly two different microbridge heater elements (e.g., using one or two sensing circuits 100 of FIG. 1) to two different temperature levels. Thus, as illustrated at block 202, a first thermal conductivity signal of a vapor-air mixture at a first temperature and a second thermal conductivity signal at a second temperature can be determined. Next, as indicated at block 204, a ratio of the two obtained signals can be formed. Note that such a ratio may be referred to generally as a "vapor ratio." Thus, a vapor ratio of said first thermal conductivity signal to said second thermal conductivity signal is calculated, as depicted at block 204.

The first and/or second thermal conductivity signals may simply be heater signals. For example, a heater signal may simply be the voltage if controlled to operate at approximately constant temperature rise or constant current or constant power, or the heater signal may be a current if controlled to operate at constant voltage, or approximately constant temperature rise or constant power. Those skilled in the art can appreciate that variations to the methodology described above can be implemented, while still falling within the scope and spirit of the claims set forth herein. For example, two matched heater resistors can be utilized to obtain the aforementioned two temperatures instead of sequencing with a single heater. For instance, on an airflow sensor chip, one may utilize $R_u$ at 200° C. temperature rise and $R_d$ at a 100° C. temperature rise.

Thereafter, as illustrated at block 206, the vapor ratio can be compared to a ratio obtained for air without the fuel vapor but measured or interpolated for the same ambient temperature, preferably done once and stored in a microprocessor. Note that such a ratio of air without the vapor can generally be referred to herein as an "air ratio" or "air signal ratio." Thus, as indicated at block 206, the vapor ratio can be compared to the air ratio (i.e., air without the vapor) at said first temperature and said second temperature to obtain a signal thereof.

As illustrated next at blocks 208 and 210, signal (S) can then be determined, which is based on the formulation $S=[V_{h,H}(M,T)/V_{h,L}(M,T)]-[V_{h,H}(A,T)/V_{h,L}(A,T)]$. Thereafter, as depicted at block 212, the obtained signal S can be compared to an alarm set-point near or below the LEL, which for a number of fuels is in the 0.001–0.002 ranges, if the two chosen measurement temperatures are at 100 and 200° C. above ambient. Thus, as illustrated at block 212 the signal S is compared to the alarm set-point value to thereby determine whether said vapor comprises a flammable vapor.

Note generally that the variable $V_h$ represents the heater voltage to raise heater to a relatively high temperature, H, of, for example, $\Delta T_h=200°$ C. or to a relatively low temperature, L, of, for example, $\Delta T_h=100°$ C. The variable M is generally indicative of vapor-air mixture. The variable A is generally indicative of pure, reference air. The variable T is generally indicative of ambient temperature dependence. This ambient temperature dependence can be measured simultaneously or subsequently. The ambient temperature can thus be sensed so that the proper "air" ratio signal can be selected or interpolated. In a "maximum accuracy" embodiment of the present invention, for example, the alarm set-point's small temperature dependence can be taken into account by a second look-up table that is stored in an associated microprocessor. Note also that for the calculation of the two-temperature signals it can be assumed that the micro-environmental temperature around a microbridge heater associated with the microbridge circuit (e.g., sensing circuit 100 of FIG. 1), when heated to 100 or 200° C. above ambient can average out to be at 50 and 100° C. above ambient, respectively, regardless of the value of the ambient temperature, which can be varied from −40 to 60° C.

Figure 4:
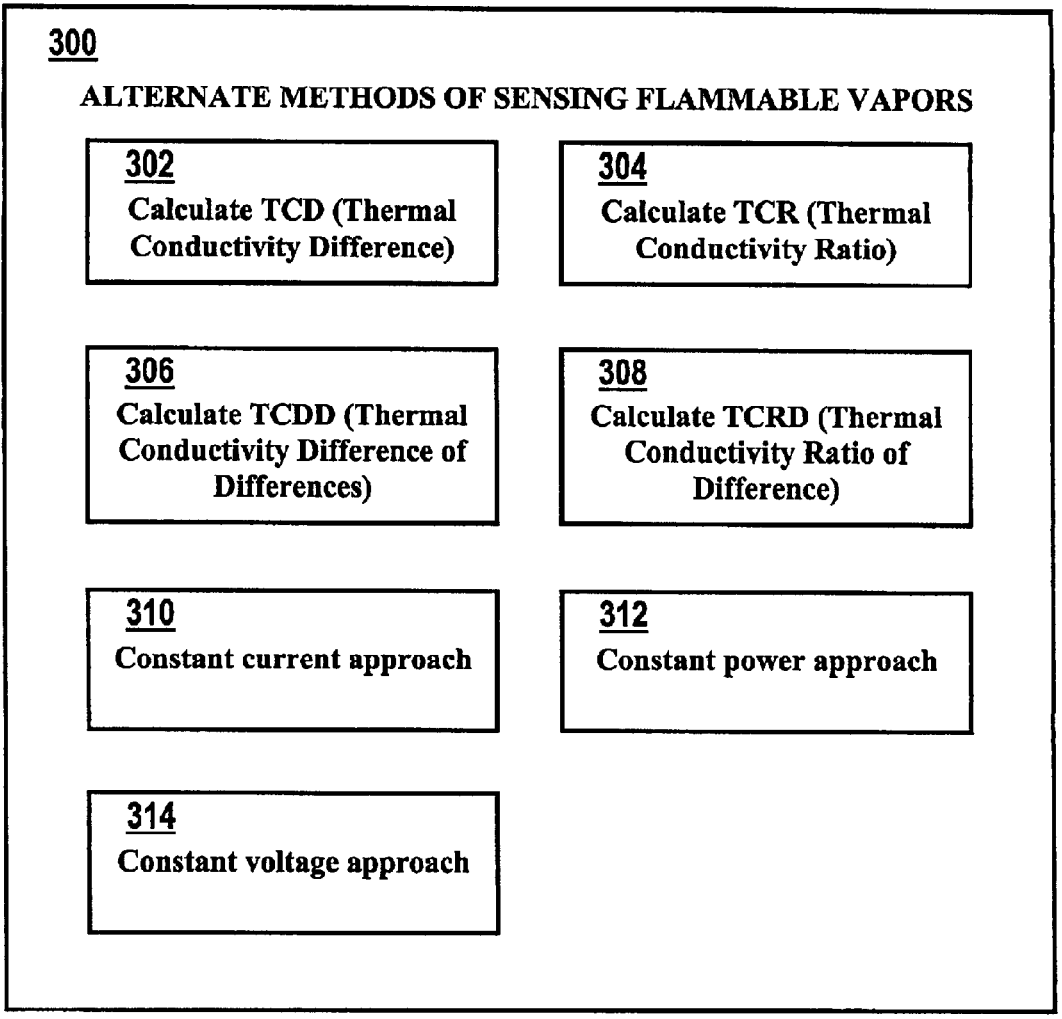
FIG. 4 depicts a high-level block diagram illustrating alternative methods for sensing flammable vapors via thermal conductivity measurements, in accordance with alternative embodiments of the present invention.

FIG. 4 depicts a high-level block diagram 300 illustrating alternative methods for sensing flammable vapors via thermal conductivity measurements, in accordance with alternative embodiments of the present invention. As indicated at block 302, a TCD (Thermal Conductivity Difference) approach may be implemented by calculating the TCD between the TC of air and that of the sensed TC. Storing the temperature-dependent TC of reference air in a microprocessor look-up table can minimize LEL alarm set-point temperature dependence.

This approach is relatively simple; however, a microprocessor is still generally required to eliminate the strong temperature dependence from the combined effects of TC, electronic and sensor offsets, and Pt-resistance. Note that some gases, such as methane and natural gases, have TCs larger than air, rather than smaller as most common fuel vapors and possibly alcohols do. Note that, according to the method described at block 302, S(302) can be ≧10 mV. It should be understood by those skilled in the art that such values are merely suggested parameters and do not constitute a limiting feature of the present invention.

As indicated at block 304, a Thermal Conductivity Ratio (TCR) sensing approach can be implemented by calculating the TCR between the TC of air over that of the sensed TC of the gas mixture. According the TCR approach illustrated at block 304, the LEL alarm set-point temperature dependence can be minimized (i.e., even after an optimal analog correction) by storing the temperature-dependent TC of reference air in a microprocessor look-up table. Although the approach illustrated at block 304 is a relatively simple one, a microprocessor is generally required to form the ratio and to eliminate the strong temperature dependence from the combined effects of TC, electronic and sensor offsets, and Pt-resistance. Note that some gases such as methane and natural gases have TC-ratio >1, rather than <1 as most common fuel vapors and possibly alcohols. Additionally, LEL alarm set-point can be S(304)≧1+0.003. It should be understood by those skilled in the art that such values are merely suggested parameters and do not constitute a limiting feature of the present invention.

As illustrated at block 306, a Thermal Conductivity Difference of Differences (TCDD) approach can also be implemented by calculating the difference in the sensed TC-signals at high and low heater temperatures minus the same difference for air. This approach minimizes the temperature dependence of LEL alarm set-point (i.e., even after an optimal analog correction) by storing the temperature-dependent difference signals of reference air in a microprocessor look-up table.

One advantage of this approach stems from a lower temperature dependence of the LEL alarm point, which may not be obtained utilizing either the TCD or TCR approaches previously described. Note that there is a large difference in signals between small-molecule fuels such as methane and large-molecule fuels. In general, the LEL alarm set-point can be obtained for S(306)≧2 mV. It should be understood by those skilled in the art that such values are merely suggested parameters and do not constitute a limiting feature of the present invention. Thus, the first and second thermal conductivity signals can be utilized to determine a combustible gas-in-air concentration of an air-fuel mixture that is approximately equal or near (i.e., smaller, equal, larger) to a lower-explosive limit (LEL) of said air-fuel mixture.

As depicted at block 308, a Thermal Conductivity Ratio Difference (TCRD) approach can be implemented by calculating the TCRD between the ratios in the sensed TC-signals at high and low heater temperatures minus the same ratio for air. This approach offers the smallest temperature dependence and fuel-vapor dependence of the alarm set-point, although a microprocessor is still needed to eliminate the strong temperature dependence from the combined effects of TC, electronic and sensor offsets, and Pt-resistance.

There still exists, however, a significant difference in signals between small-molecule fuels such as methane and large-molecule fuels. The LEL alarm set-point can be obtained by S≧0.0008. It should be understood by those skilled in the art that such values are merely suggested parameters and do not constitute a limiting feature of the present invention. Note that the TCRD approach is a preferred approach for implementing the method and apparatus of the present invention. A thermal conductivity ratio difference (TCRD) mechanism can thus be utilized for determining whether the vapor comprises a flammable vapor by evaluating a TCRD between a ratio of at least two sensed thermal conductivity signals at a high heater temperature and a low heater temperature minus an analogous ratio associated with the air without the vapor.

Several other approaches are also generally illustrated in FIG. 4, including a "constant current" approach, as indicated at block 310, a "constant power" approach, as illustrated at block 312, and a "constant voltage" approach, as indicated at block 314. A microbridge heater control circuit, for example, can be utilized with a "constant current" approach to produce output voltage signals, which are utilized to sense combustible vapor. The constant current approach is described in greater detail herein with respect to block 412 of FIG. 5.

All of the approaches described herein can use a look-up table of the temperature-dependent TC, ΔTC or TC-ratio to minimize the temperature dependence of the corresponding signal, S(3xx). Only the TCRD approach, however, can be used without a temperature-dependent alarm point or one that is minimally dependent on temperature. To compare these four approaches, signal data vs. temperature and vs. type of fuel can be computed by assuming sensor operation with the highest possible heater temperature to minimize offset effects of individual sensors and electronic components, e.g., $\Delta T_h = 200°$ C. for TCD and TCR approaches and $\Delta T_h = 100°$ C. for the second temperature level for the TCDD and TCRD approaches and nominal heater voltage of 4.000 V in air at 20° C.

By way of summary, and to show the relative merits of the TCRD approach against the other approaches described herein, the maximum signal variabilities ratioed to the average signals are listed below in Table 3, which are simulated vapor sensor outputs at the LEL levels: a. Versus temperature and b. Versus fuel types from propane to octane.

TABLE 3

Maximum Vapor Sensor Output Variabilities vs. Sensing Method Variabilities Expressed as a Ratio $\Delta S_{max}/S$

| Method | −40 to 60° C. | Propane-Octane | Comments |
| --- | --- | --- | --- |
| TCD | 1.50 | 1.08 | Simplest method, but has largest temp and fuel dependence of LEL signal. |
| TCR | 0.60 | 1.27 | Signals for methane, ethane & alcohols <0, others >0 relative to air. |
| TCDD | 0.26 | 0.88 | Methane signal at LEL is ~2x larger than that for butane. |
| TCRD | 0.13 | 0.73 | Most stable output at LEL, and may not Require temperature compensation of alarm point. Also applicable to methane, natural gas, ethane and alcohols. |

Clearly, the TCRD method is a preferred approach. As shown, the TCRD method exhibits the least relative variability, which is desirable so that the chosen alarm set-point is as close as possible to the same LEL level to as many fuels and over as wide a temperature range as possible. For $\Delta T_{h,L} = 100$ and $\Delta T_{h,H} = 200°$ C., the change in the TCRD is typically ≧0.1% relative to air, for LEL vapor concentrations of fuels with less than 7 carbon atoms and for the listed temperature range. The higher the temperature and the temperature difference, the larger and more useful will the signal to noise ratio (but a balance to prevent against sensor drift if too high).

Note that the concept of utilizing the speed of sound or thermal conductivity to sense the stoichiometry of gasoline-vapor-air mixtures has been previously implemented and sensor samples thereof have been constructed and sold commercially. Additionally, the concept of utilizing the temperature dependence of TC to characterize fuel properties has also been considered for determining the oxygen demand, $D_{O2}$, of a fuel such as natural gas, LPG or fuel oil, but only in the context of TC ratios or ΔTCs, embedded in correlation algorithms to derive $D_{O2}$, and not to determine the LEL of fuel vapors in air, and much less in the form of a TCRD sensor.

Figure 5:
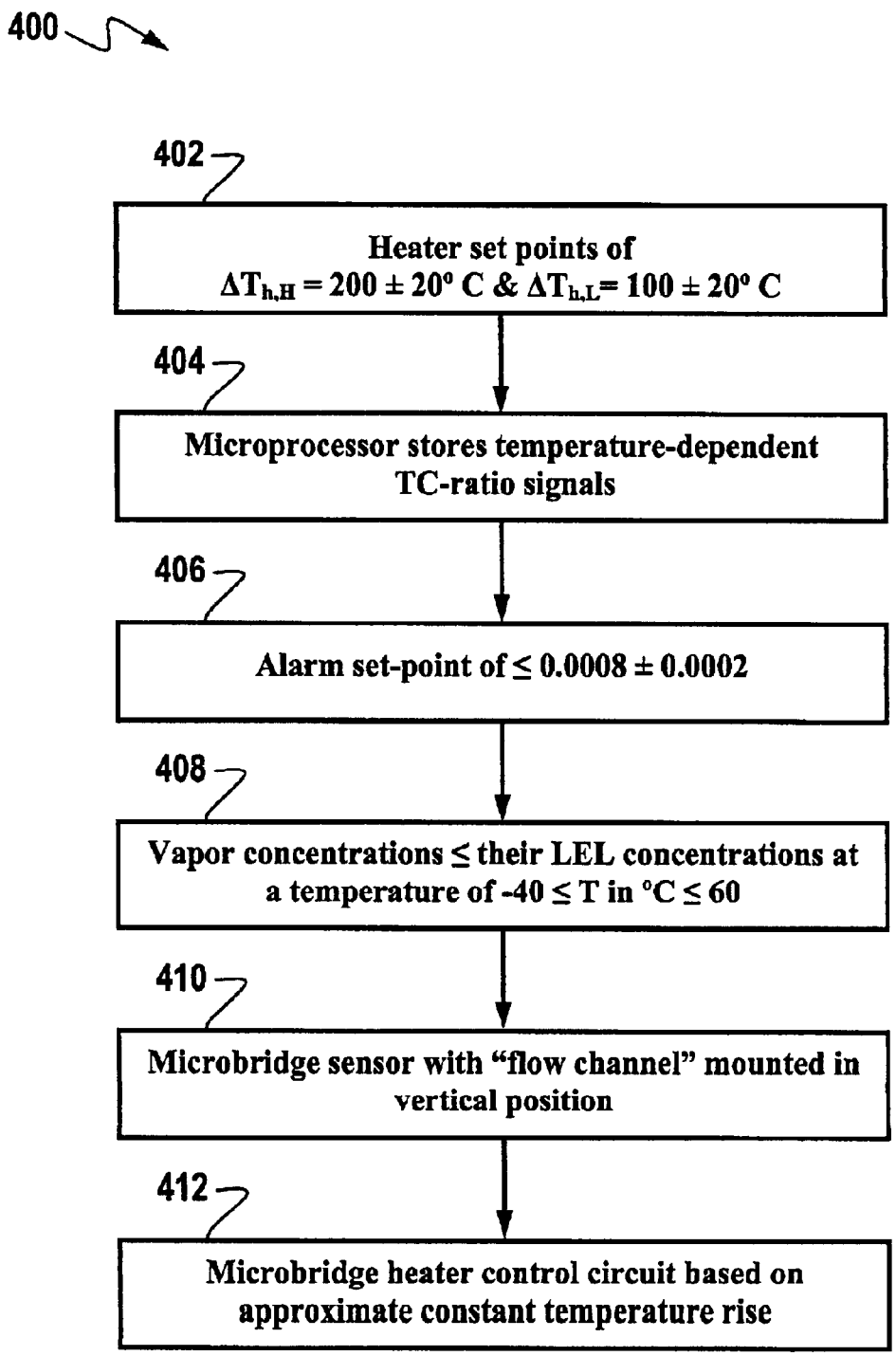
FIG. 5 illustrates a flow-chart of operations illustrating parameters for a sensor design based on the TCRD method, which may be implemented in accordance with alternative embodiments of the present invention.

FIG. 5 illustrates a flow-chart 400 of operations illustrating parameters for a sensor design based on the TCRD method, which may be implemented in accordance with a preferred embodiment of the present invention. Note that the methodology and steps indicated in FIG. 5 represent but one possible logical flow of operations that may be implemented in accordance with a preferred embodiment of the present invention. Alternative embodiments of the present invention may be implemented, for example, with similar operational steps arranged in a different order. Thus, according to FIG. 5, a sensor design can be designed based on the TCRD approach described herein.

As depicted at block 402, heater sets points of $\Delta T_{h,H} = 200 \pm 20°$ C. and $\Delta T_{h,L} = 100 \pm 20°$ C. can be implemented. As indicated next at block 404, a microprocessor can be utilized to store the temperature-dependent TC-ratio signals for $\Delta T_h = 100$ and 200° C. for reference air. As illustrated thereafter at block 406, an alarm set-point of ≦0.0008±0.0002 can be implemented, representing as indicated at block 408, vapor concentrations, which are greater, equal or less than their LEL concentrations at a temperature range of approximately $-40 \leq T$ in ° C. ≦60. As indicated next at block 410, the microbridge sensor can be configured with its "flow channel" mounted in the vertical position to enable natural convection to purge a sample gas to an associated sensing chip.

Finally, as depicted at block 412, an associated microbridge heater control circuit can be utilized to generate a maximum (e.g., ~2× larger than the presently used "constant temperature-rise approach") and easy-to-process output voltage signals, unless other considerations (e.g., development cost, most familiarity, approximately self-regulating, etc.) demand that the well-practiced "modified constant temperature rise approach" be used, which comprises adjusting the $R_r/R_c$ ratio in such a manner that the $V_1$ or $V_2$ signal variations (i.e., see FIG. 1) with ambient temperature are minimized, as mentioned above. A "constant current" approach, as described herein, however, may also be utilized to generate such output voltage signals. The modified "constant temperature rise approach" is preferred, so that the heater voltage is as independent of ambient temperature as possible, in air.

Note that the approach described above may have certain limitations. However, the appearance of large concentrations of $H_2O$ above 7% and/or $CO_2$ above 4% (e.g., as in a fire) can also reach a signal level that is near or above the alarm set-point, which may not be undesirable. Those skilled in the art can thus appreciate that method and apparatus described herein can be applied to a variety of sensor applications. For example, the sensor described herein may comprise a fire-safety sensor, by virtue of its ability to sense the appearance of large concentrations of $H_2O$ above 7% and/or $CO_2$ above 4% (e.g., as in a fire), which can reach a signal level that is near or above the flammable gas alarm set-point.

The present invention offer a fast, reliable, sensitive, low-power, low-cost, low-false-alarm, ambient-conditionindependent sensor of non-specific, flammable organic fuel vapors based on sensing certain bulk thermal conductivity properties of air when containing small amounts of such vapors. The preferred approach for the sensor operation is the TCRD approach. The concept and use of the TCRD approach generally includes the step of sensing the TC properties of air at two temperatures, forming their ratio and comparing it to the same ratio when fuel vapors are not present. The underlying physics is the higher TC-temperature dependence of organic fuels, including methane, ethane, alcohols, water vapor and carbon dioxide than that of air.

Additionally, the TCRD sensing operation can be performed utilizing one of a variety of possible circuit-design approaches, which controls the sensor heater based on a constant input current (i.e., sometimes preferred because of largest signal and output in the form of a voltage), constant input voltage, constant absolute temperature, constant temperature rise, constant power or a constant optimized temperature rise. Note that such a constant optimized temperature rise approach is advantageous, because of the nature of its self-regulating input voltage and relative independence from ambient temperature variations.

Those skilled in the art should appreciate that the present invention can be implemented in a number of applications besides the flammable vapor sensor described earlier. For example, the sensor method and apparatus described herein can be implemented as a stoichiometry sensor to sense fuel-air mixture ratios before combustion or as a smoke/fire sensor by virtue of its sensitivity to $CO_2$ and $H_2O$, whereby the alarm set-points are reached individually by $CO_2$ at ~4 vol. % and $H_2O$ at ~7 vol. %. In another application of the TC sensing technology, a correction method can be implemented thereof to eliminate the interference of $H_2O$ and $CO_2$ in TC-based $H_2$ sensors.

The present invention can also be implemented as a low-cost, microbridge-based sensor for homes to detect the presence of flammable gases or vapors at concentrations at or below their lower explosive limit (LEL) in the vicinity of pilot flames of water heaters so that these pilot flames can be shut off before risking ignition of the vapor cloud. Additionally, the sensor described herein may be implemented in the context of an application having a shut-off fuel valve, again, as a low-cost, microbridge-based sensor for homes, to detect the presence of flammable gases or vapors.

The present invention offers a number of advantages over the prior art. In particular, the TCRD sensor approach described herein offers various advantages over prior art fuel vapor sensing approaches. The TCD, TCR, TCDD and TCRD sensing approaches are not specific to any fuel vapor (i.e., even less specific than metal oxide, electrochemical, swelling polymer or NDIR sensors) and are based on the fact that the TC or the TC's temperature dependence of vapor-air mixtures are different from those of air. One draw-back of the TCRD approach is that the TCRD approach does not respond to CO or $H_2$. However, the difference in TCRD signals between an air-organic fuel vapor mixture and air is a fair measure of its stoichiometry or flammability, which is not true for sensor signals from metal oxide, electrochemical or optical absorption sensing methods for such a wide range of fuels.

Additionally, catalytic or surface activity (i.e., prone to poisoning as with Pellistor and metal oxide-based sensors) is not used in any form for the operation of this TCRD sensor. Digital temperature compensation via a microprocessor-based look-up table of the TC-signal of reference air, enables the use of the sensor described herein over a wider temperature range from −40 to 60° C. than analog TC sensors. TC sensors are generally more stable than metal oxide, catalytic or optical absorption sensors and enable the reliable measurement of changes of 0.1% in the ratio of sensor heater voltages, which is typical of organic fuel vapors near their LEL. The TCRD sensing approach described herein is also generally applicable over a range of temperatures, $-40 \leq T \leq 60°$ C., for all checked fuels vapors including those with TCs higher than air, such as methane and natural gas, and those with TCs close to air, such as ethane and alcohols, which would not be true for TCD or TCR sensors.

The TCRD sensing approach described herein also can provide a more predictable sensor signal than analog TCD or TCDD approaches because of better control/cancellation of output interferences due to sensor asymmetries and electronics-dependent offsets and, therefore, reduces the cost of calibration. The TCRD sensing approach described herein also offers shorter response times than metal oxide, Pellistor or electrochemical sensing approaches, which is important for detection of fuel vapors generated near a furnace with a standing-pilot flame after spilling liquid fuel or any other combustible liquid such as a solvent or paint. The TCRD sensing approach described herein also does not have to contend with the pressure changes and associated small changes in TC of the sealed reference chamber, as used by prior art differential TC sensor approaches.

Packaging the sensor described above in a fashion that facilitates user-friendliness, affordability and fast response, long and stable service life, and sensing accuracy is not a trivial matter. Two preferred approaches are thus described herein. One approach is directed toward indoor use, while another is directed toward outdoor use. The indoor package can be configured, as indicated above, by an off-the-shelf Honeywell AWM3100 type mass air flow sensor package (i.e., after adding microprocessor circuitry), with the flow tube held in a close-to-vertical position to take advantage of natural convection purge, as induced by the heater element on the microbridge structure.

Figure 6:
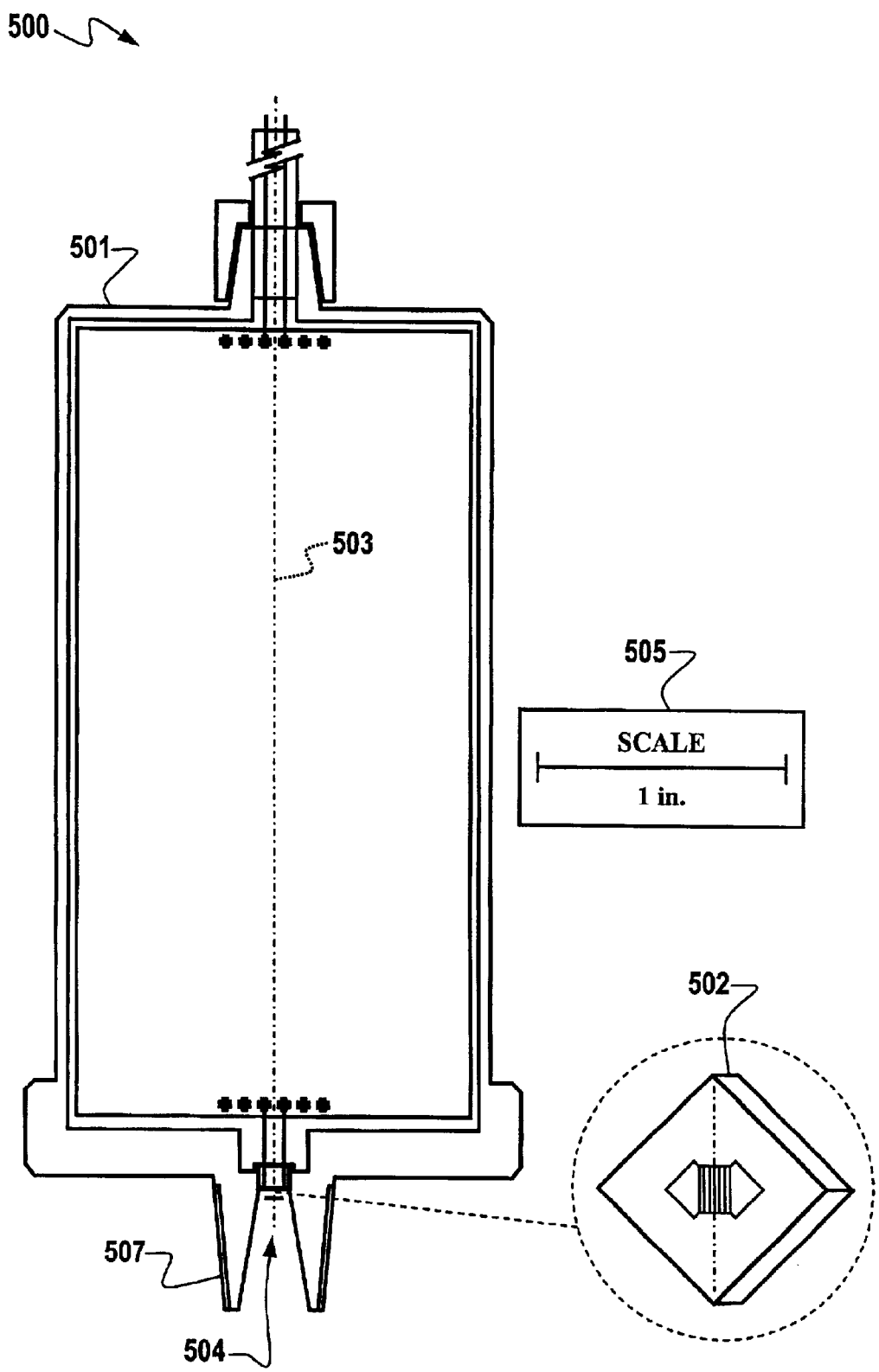
FIG. 6 depicts a sensor package in which an embodiment of the present invention may be implemented.

FIG. 6 depicts a sensor package 500 in which an embodiment of the present invention can be implemented. Sensor package 500 generally comprises a housing 501 and an area 504 in which a sensor chip 502 may be located. Note that sensor package 500 illustrated in FIG. 6 is based on a 1-inch scale 505. Sensor package 500 can be adapted for "outdoor" or "indoor" use. Sensor package 500 may be utilized for outdoor use. Sensor package 500 can be configured according to the microsensor housing configuration described and illustrated in U.S. Pat. No. 6,322,247 to Bonne et al., entitled "Microsensor Housing". (Note that U.S. Pat. No. 6,322,247 is incorporated herein by reference.)

It can be appreciated by those skilled in the art that sensor package 500 can be configured to include digitization and microprocessor circuitry. The housing 501 can be positioned with its axis 503 in a vertical position, sensor facing down, such that the sensor element (i.e., sensor chip 502) is protected against interference from airflows by a special baffle 507, which is also described in U.S. Pat. No. 6,322,247. A baffle 507 of this type can be configured as a single-stage baffle, which is generally shaped to facilitate liquid runoff via the sides, if liquid should get near sensor chip 502. The baffle may be machined with a set of concentric holes projecting an area around sensor chip 502 to inhibit direct splashes from the direction of the fitting to hit the sensor chip 502. Baffle 507 can provide sensor chip 502 protection while permitting diffusional access of fluid to sensor chip 502 from all sides.

Those skilled in the art can appreciate that the use of the device depicted in U.S. Pat. No. 6,322,247, including the baffle configuration thereof, is not considered a limiting feature of the present invention, but merely represents one possible sensor package in which the present invention can be embodied. Other variations are of course possible, including baffle modifications thereof, while still falling within the scope and spirit of the invention described and claimed herein.

The embodiments and examples set forth herein are presented to best explain the present invention and its practical application and to thereby enable those skilled in the art to make and utilize the invention. Those skilled in the art, however, will recognize that the foregoing description and examples have been presented for the purpose of illustration and example only. Other variations and modifications of the present invention will be apparent to those of skill in the art, and it is the intent of the appended claims that such variations and modifications be covered. For example, it can be appreciated by those skilled in the art that the present invention described herein can apply to varied applications, such as for example, automotive engine combustion or cabin air quality control, sensing fugitive emissions at chemical process plants and combustible gas sensing in home or commercial conditioned space. The present invention may also be implemented without the use of a microprocessor. For example, an analog-based approach may be implemented to obtain a TCRD signal or alarm a sensor trigger under relevant TCRD conditions.

The description as set forth is thus not intended to be exhaustive or to limit the scope of the invention. Many modifications and variations are possible in light of the above teaching without departing from the scope of the following claims. It is contemplated that the use of the present invention can involve components having different characteristics. It is intended that the scope of the present invention be defined by the claims appended hereto, giving full cognizance to equivalents in all respects.

The embodiments of an invention in which an exclusive property or right is claimed are defined as follows:

1. A method for sensing a flammable vapor, said method comprising the steps of:
    determining a first thermal conductivity signal of a vapor at a first temperature and a second thermal conductivity signal at a second temperature;
    calculating a vapor signal ratio of said first thermal conductivity signal to said second thermal conductivity signal;
    comparing said vapor signal ratio to an air signal ratio of air without said vapor at said first temperature and said second temperature to obtain a calculated signal thereof; and
    thereafter comparing said calculated signal to an alarm set-point value to thereby determine whether said vapor comprises a flammable vapor.

2. The method of claim 1 wherein the step of comparing said calculated signal to an alarm set-point value, further comprises the step of:
    comparing said calculated signal to said alarm set-point value, wherein said alarm set-point value is located in a range of values near a lower-explosive limit (LEL).

3. The method of claim 1 wherein the step of comparing said calculated signal to an alarm set-point value, further comprises the step of:
    comparing said calculated signal to said alarm set-point value, wherein said alarm set-point value is located in a range of values below a lower-explosive limit (LEL).

4. The method of claim 1 wherein the step of determining a first thermal conductivity signal of a vapor at a first temperature and a second thermal conductivity signal at a second temperature, further comprises the step of:
    determining said first thermal conductivity signal of a vapor at a first temperature and said second thermal conductivity signal at a second temperature, wherein said first temperature comprises 100° C. above ambient and said second temperature comprises 200° C. above ambient.

5. The method of claim 1 wherein the step of determining a first thermal conductivity signal of a vapor at a first temperature and a second thermal conductivity signal at a second temperature, further comprises the step of:
    determining said first thermal conductivity signal of said vapor at said first temperature and said second thermal conductivity at a second temperature utilizing a microbridge sensor.

6. The method of claim 5 further comprising the step of:
    configuring said microbridge sensor to comprise at least one microbridge heater.

7. The method of claim 6 further comprising the steps of:
    initially heating said microbridge sensor to said first temperature; and
    thereafter heating said microbridge sensor to said second temperature.

8. The method of claim 1 wherein the step of comparing said calculated signal to an alarm set-point value to thereby determine whether said vapor comprises a flammable vapor, further comprises the step of:
    determining a combustible gas-in-air concentration of an air-fuel mixture that is approximately equal to a lower-explosive limit (LEL) of said air-fuel mixture utilizing said first and second thermal conductivity signals.

9. The method of claim 8 wherein said combustible gas comprises an organic vapor of a fuel associated with said combustible gas-air mixture.

10. The method of claim 8 wherein said combustible gas comprises an organic vapor of a solvent associated with said combustible gas-air mixture.

11. The method of claim 1 further comprising the step of:
    calculating said signal according to a formula $S=V_{h,H}(M,T)/V_{h,L}(M,T)-V_{h,H}(A,T)/V_{h,L}(A,T)$, wherein S represents said signal, T represents a temperature, M represents a flammable vapor mixture, A represents air, h represents a heater, H represents a high heater temperature, L represents a low heater temperature, and V represents a heater voltage required to maintain a balance of an associated Wheatstone bridge circuit.

12. The method of claim 1 further comprising the step of:
    determining whether said vapor comprises a flammable vapor by evaluating a thermal conductivity difference (TCD) between a thermal conductivity of said air without said vapor to a thermal conductivity of said vapor.

13. The method of claim 1 further comprising the step of:
    determining whether said vapor comprises a flammable vapor by evaluating a thermal conductivity ratio (TCR) between a thermal conductivity of air without said vapor to that of a sensed thermal conductivity of a gas mixture associated with said vapor.

14. The method of claim 1 further comprising the step of:
    determining whether said vapor comprises a flammable vapor by evaluating thermal conductivity difference of differences (TCDD) between a difference in at least two sensed thermal conductivity signals at a high heater temperature and a low heater temperature minus an analogous difference associated with said air without said vapor.

15. The method of claim 1 further comprising the step of: determining whether said vapor comprises a flammable vapor by evaluating a thermal conductivity ratio difference (TCRD) between a ratio of at least two sensed thermal conductivity signals at a high heater temperature and a low heater temperature minus an analogous ratio associated with said air without said vapor.

16. The method of claim 1 further comprising the steps of: determining said air signal ratio of air without said vapor at said first temperature and said second temperature; and thereafter storing said air signal ratio within a storage area of a microprocessor.

17. The method of claim 16 further comprising the step of: retrieving an air signal ratio value from said storage area of said microprocessor, wherein said air signal ratio value is obtained by interpolating between a plurality of tabulated values and values corresponding to a measured ambient temperature, prior to comparing said vapor signal ratio to said air signal ratio to obtain said signal thereof.

18. A method for sensing a flammable vapor, said method comprising the steps of:

determining a first thermal conductivity signal of a vapor at a first temperature and a second thermal conductivity signal at a second temperature utilizing a microbridge sensor configured to comprise at least one microbridge heater;

calculating a vapor signal ratio of said first thermal conductivity signal to said second thermal conductivity signal;

comparing said vapor signal ratio to an air signal ratio of air without said vapor at said first temperature and said second temperature to obtain a calculated signal thereof, wherein said calculated signal is calculated according to a formula $S=V_{h,H}(M,T)/V_{h,L}(M,T)-V_{h,H}(A,T)/V_{h,L}(A,T)$, wherein S represents said signal, T represents a temperature, M represents a flammable vapor mixture, A represents air, h represents a heater, H represents a high heater temperature, L represents a low heater temperature, and V represents a heater voltage; and thereafter comparing said calculated signal to an alarm set-point value to thereby determine whether said vapor comprises a flammable vapor.

19. An apparatus for sensing a flammable vapor, said apparatus comprising:

a sensor for determining a first thermal conductivity signal of a vapor at a first temperature and a second thermal conductivity signal at a second temperature;

a calculation mechanism for calculating a vapor signal ratio of said first and second thermal conductivity signals;

a first comparator for comparing said vapor signal ratio to an air signal ratio of air without said vapor at said first temperature and said second temperature to obtain a calculated signal thereof; and a second comparator for comparing said calculated signal to an alarm set-point value to thereby determine whether said vapor comprises a flammable vapor.

20. The apparatus of claim 19 wherein alarm set-point value is located in a range of values near a lower-explosive limit (LEL).

21. The apparatus of claim 19 wherein said alarm set-point value is located in a range of values below a lower-explosive limit (LEL).

22. The apparatus of claim 19 wherein said first temperature comprises approximately 100° C. above ambient and said second temperature comprises approximately 200° C. above ambient.

23. The apparatus of claim 19 wherein said sensor comprises:

a resistive heater element located on a thermally insulated, self-supporting microbridge structure;

a resistive temperature sensing element located on a thermally grounded sensor chip substrate; and a resistive reference element located on said thermally grounded sensor chip substrate.

24. The apparatus of claim 23 further comprising:

a heating mechanism for heating at least one microbridge heater element.

25. The apparatus of claim 24 further comprising:

heating mechanism for heating said microbridge sensor to said first temperature and said second temperature.

26. The apparatus of claim 19 wherein said first and second thermal conductivities determine a combustible gas-in-air concentration of a mixture that is less than or greater than or approximately equal to a lower-explosive limit (LEL) of a combustible gas thereof.

27. The apparatus of claim 26 wherein said mixture comprises an organic vapor associated with a fuel associated with said air-fuel mixture.

28. The apparatus of claim 19 wherein said signal is calculated according to a formula $S=V_{h,H}(M,T)/V_{h,L}(M,T)-V_{h,H}(A,T)/V_{h,L}(A,T)$, wherein S represents said signal, T represents a temperature, M represents a flammable vapor mixture, A represents air, h represents a heater, H represents a high heater temperature, L represents a low heater temperature, and V represents a heater voltage required to maintain a balance of an associated Wheatstone bridge circuit.

29. The apparatus of claim 19 further comprising:

a thermal conductivity difference (TCD) mechanism for determining whether said vapor comprises a flammable vapor by evaluating a TCD between a thermal conductivity of said air without said vapor to a thermal conductivity of said vapor.

30. The apparatus of claim 19 further comprising the step of:

a thermal conductivity ratio (TCR) mechanism for determining whether said vapor comprises a flammable vapor by evaluating a TCR between a thermal conductivity of air without said vapor to that of a sensed thermal conductivity of a gas mixture associated with said vapor.

31. The apparatus of claim 19 further comprising:

a thermal conductivity difference of differences (TCDD) mechanism for determining whether said vapor comprises a flammable vapor by evaluating a TCDD between a difference in at least two sensed thermal conductivity signals at a high heater temperature and a low heater temperature minus an analogous difference associated with said air without said vapor.

32. The apparatus of claim 19 further comprising:

a thermal conductivity ratio difference (TCRD) mechanism for determining whether said vapor comprises a flammable vapor by evaluating a TCRD between a ratio of at least two sensed thermal conductivity signals at a high heater temperature and a low heater temperature minus an analogous ratio associated with said air without said vapor.

33. The apparatus of claim 19 further comprising:

a microprocessor having a storage area therein, wherein said air signal ratio is stored for a plurality of values within an ambient temperature range.

34. The apparatus of claim 19 wherein said sensor comprises a fire-safety sensor.

35. An apparatus for sensing a flammable vapor, said apparatus comprising:

a microbridge sensor for determining a first thermal conductivity signal of a vapor at a first temperature and a second thermal conductivity signal at a second temperature, wherein said microbridge sensor comprises at least one microbridge heater;

a calculation mechanism for calculating a vapor signal ratio of said first thermal conductivity signal to said second thermal conductivity signal;

a first comparator for comparing said vapor signal ratio to an air signal ratio of air without said vapor at said first temperature and said second temperature to obtain a calculated signal thereof, wherein said calculated signal is calculated according to a formula $S=V_{h,H}(M,T)/V_{h,L}(M,T)-V_{h,H}(A,T)/V_{h,L}(A,T)$, wherein S represents said signal, T represents a temperature, M represents a flammable vapor mixture, A represents air, h represents a heater, H represents a high heater temperature, L represents a low heater temperature, and V represents a heater voltage; and a second comparator for comparing said calculated signal to an alarm set-point value to thereby determine whether said vapor comprises a flammable vapor.

* * * * *